(12) United States Patent
Varieur et al.

(10) Patent No.: US 6,174,335 B1
(45) Date of Patent: Jan. 16, 2001

(54) ALIGNMENT GUIDE FOR SLOTTED PROSTHETIC STEM

(75) Inventors: Michael S. Varieur, Attleboro; Pierre S. Ostiguy, Jr., Rochester; Charles W. Jaggers, Mansfield; Paul Salvas, Norton; Mark Allan Manasas, S. Easton, all of MA (US)

(73) Assignee: Johnson & Johnson Professional, Inc., Raynham, MA (US)

( * ) Notice: Under 35 U.S.C. 154(b), the term of this patent shall be extended for 0 days.

(21) Appl. No.: 09/130,396

(22) Filed: Aug. 6, 1998

Related U.S. Application Data

(63) Continuation-in-part of application No. 09/102,721, filed on Jun. 22, 1998, which is a continuation-in-part of application No. 08/772,630, filed on Dec. 23, 1996, now abandoned.

(51) Int. Cl.[7] ............................. A61F 2/32; A61B 17/00
(52) U.S. Cl. ..................... 623/22.12; 606/99; 623/908
(58) Field of Search ..................... 623/18, 20, 22, 623/23, 22.12, 23.35, 902, 908; 606/86–90, 95, 96, 99

(56) References Cited

U.S. PATENT DOCUMENTS

| | | | |
|---|---|---|---|
| 4,347,845 | * | 9/1982 | Mayfield ............................ 606/86 |
| 4,738,256 | * | 4/1988 | Freeman et al. .................... 606/87 |
| 4,765,328 | * | 8/1988 | Keller et al. ........................ 623/18 |
| 5,409,492 | * | 4/1995 | Jones et al. ......................... 606/86 |
| 5,480,453 | * | 1/1996 | Burke .................................. 623/23 |
| 5,609,642 | * | 3/1997 | Johnson et al. .................... 623/20 |
| 5,702,463 | * | 12/1997 | Pothier et al. ...................... 623/20 |
| 5,755,802 | * | 5/1998 | Gerber ................................ 623/20 |
| 5,785,707 | * | 7/1998 | Boyd et al. ......................... 606/96 |
| 5,800,437 | * | 9/1998 | Gustilo et al. ..................... 606/86 |
| 5,849,015 | * | 12/1998 | Haywood et al. .................. 606/99 |

* cited by examiner

Primary Examiner—Mickey Yu
Assistant Examiner—Tram A. Nguyen
(74) Attorney, Agent, or Firm—Nutter, McClennen & Fish, LLP

(57) ABSTRACT

An alignable orthopedic prosthesis system includes a prosthesis and an alignment guide. The prosthesis includes a stem having at least one slot extending along its length. The alignment guide has an alignment body with a guide surface extending from an end thereof, namely a key element formed as a blade for engaging and guiding the slot to orient the prosthesis stem. The alignment body also fits against a machined bone surface so that the blade is positioned in a plane that is oriented to guide the stem smoothly into contact with a recess formed in the bone.

19 Claims, 10 Drawing Sheets

ALIGNMENT GUIDE FOR SLOTTED PROSTHETIC STEM

CROSS-REFERENCE TO RELATED APPLICATIONS

This application is a continuation-in-part of U.S. patent application Ser. No. 09/102,721 filed Jun. 22, 1998 entitled Alignment Guide for Fluted Prosthetic Stems, which was a continuation-in-part of U.S. patent application Ser. No. 08/772,630, filed Dec. 23, 1996 now abandoned.

STATEMENT REGARDING FEDERALLY SPONSORED RESEARCH

Not Applicable.

FIELD OF THE INVENTION

The present invention relates to an alignment guide for ensuring proper alignment or orientation of a prosthetic stem in bone.

BACKGROUND OF THE INVENTION

Stems are used in prosthetic joint implants to anchor the implant in a bone cavity. The bone for receiving the stem is typically prepared by drilling a hole in the bone and creating an opening sized and contoured to receive the stem of the implant. The stem is inserted into a prepared cavity of a bone and a joint bearing surface attached or coupled to the stem, extends out to the cavity. Many stems are fluted, i.e., they have distally extending longitudinal grooves in the stems that provide greater stability and anchoring of the stem once it is inserted into the prepared cavity.

Typically, once a fluted stem is inserted into a prepared cavity, it is extremely difficult to rotate the stem to properly reorient it. In order to do so the stem must be removed and reinserted which can damage bone and increase operative time. Typically, the stem is aligned by marking the bone and the stem and using the marks to align the stem with respect to the bone. The drawback to this method is the potential imprecision in the alignment. Because the landmark on the stem and bone are not in close proximity to each other, parallax and other problems associated with alignment by eye may result. Also, the stem may move from its aligned position as it is inserted.

Accordingly, it is an object of the present invention to provide a means for aligning a fluted stem of an orthopedic implant prior to and as it is being inserted into a prepared bone cavity.

SUMMARY OF THE INVENTION

The present invention provides a method and device for inserting a keyed or fluted prosthetic component in an aligned position into a prepared bone cavity. The bone is prepared by removing bone material from the bone canal and by machining an opening of a predetermined shape in the bone cavity. An alignment guide having an outer shape conforming with that of the machined opening is inserted into the bone cavity. The alignment guide also has an inner shape or key element corresponding to the outer shape of the fluted stem of the implant that engages the stem, preferably in a manner which provides contact with a small area of the stem. In a preferred embodiment the inner shape of the alignment guide includes notches or grooves for receiving the flutes of the stem. Another aspect of a preferred embodiment may provide protrusions in the alignment guide that make contact with certain keyed elements of the prosthesis to be inserted.

In a preferred embodiment, the alignment guide is formed generally in a broken circle or circumference to allow flexibility in removing the alignment guide. The alignment guide further comprises a means for lifting the alignment guide from the bone cavity once the stem is inserted through the alignment guide. This means may, for example, be a tab or protrusion or an opening for inserting a tool to pry out the guide. In a further embodiment, the alignment guide includes a guide body that is disposed at the distal end of a handle.

In a preferred embodiment, once the bone cavity is prepared and the alignment guide is inserted, a fluted stem of a prosthetic implant is positioned or oriented with respect to the stem axis and is then inserted into the alignment guide with the flutes extending into the notches of the alignment guide. Once the stem is inserted in the guide, the position or orientation is held true until the stem is seated into the bone cavity. As the stem is inserted, the flutes form a path within the bone cavity that the stem will generally follow during the insertion of the final segment of the stem. Once this has occurred the alignment guide may be removed by pulling the tab. The insertion is completed by extending the implant all the way into the opening until the proximal geometry of the stem is placed within the machined opening in the bone. This stem proximal geometry is also of a shape that corresponds to the machined opening so that the implant fits within the bone cavity.

In another embodiment, the alignment guide keys to the stem by a blade which fits within a longitudinal slot of the stem to fix its rotational orientation. The slot is parallel along the central plane of the spout, and the blade, which rigidly extends from the guide, is centrally aligned by means of an opposed guide surface that fits the prepared bone, so as to define an insertion orientation to guide the proximal geometry of the stem into the prepared contour. This embodiment is preferably implemented as an elongated handle, having a proximal grip portion, a blade extending from the distal end, and a middle shoulder which fits the prepared bone. Alternatively, it may be implemented as a smaller body having an outer surface portion which fits the prepared bone surface, and an inner surface portion rigidly extending in a precise plane across the prepared bone canal to engage the slotted stem.

BRIEF DESCRIPTION OF THE DRAWINGS

The invention will be more fully understood by reference to the following detailed description when considered in conjunction with the accompanying drawings, in which.

DETAILED DESCRIPTION OF THE INVENTION

Figure 1:
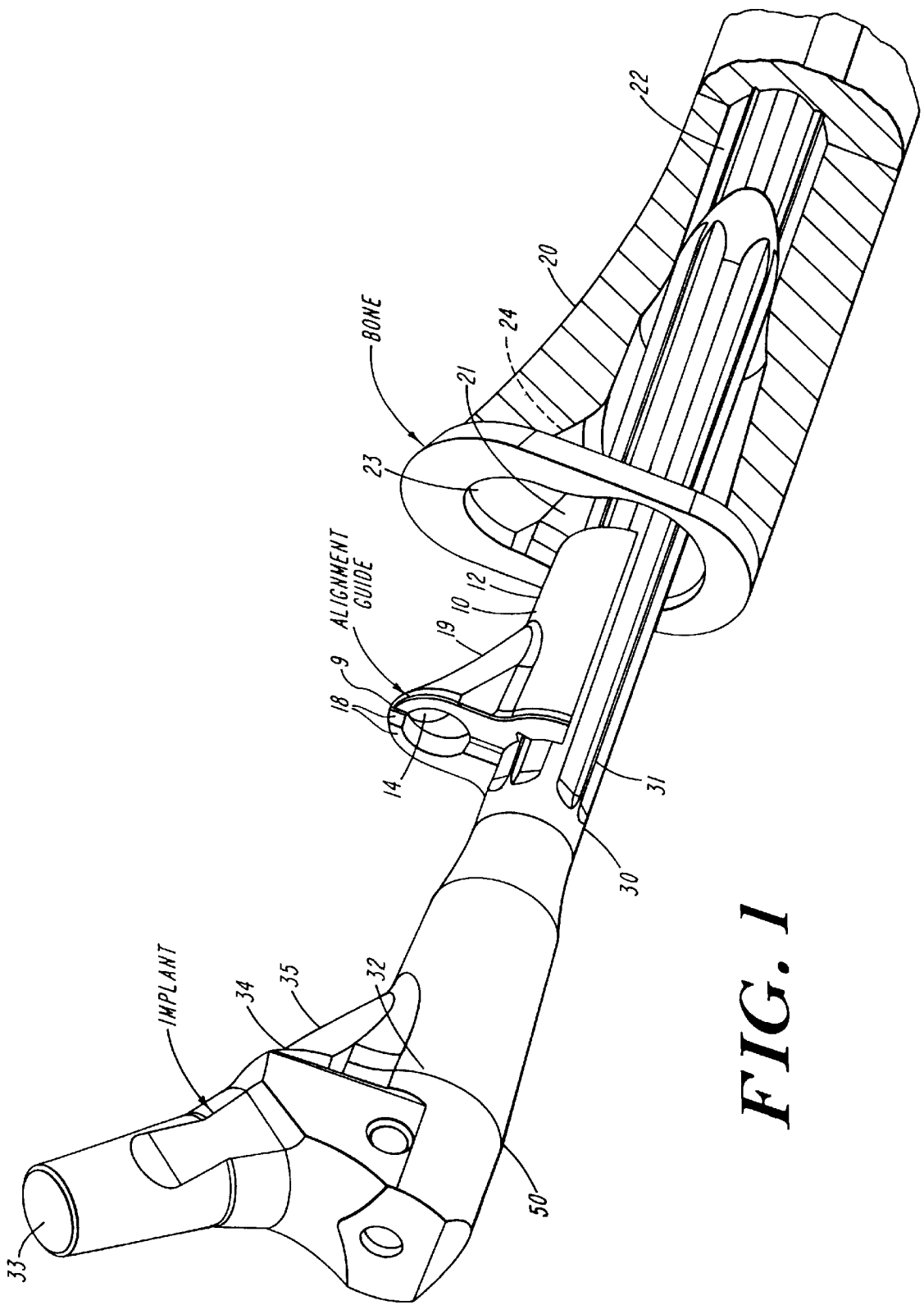
FIG. 1 illustrates an exploded perspective view of a bone with a partial break away of a prepared cavity, an alignment guide and an implant inserted through the alignment guide.
Figure 2:
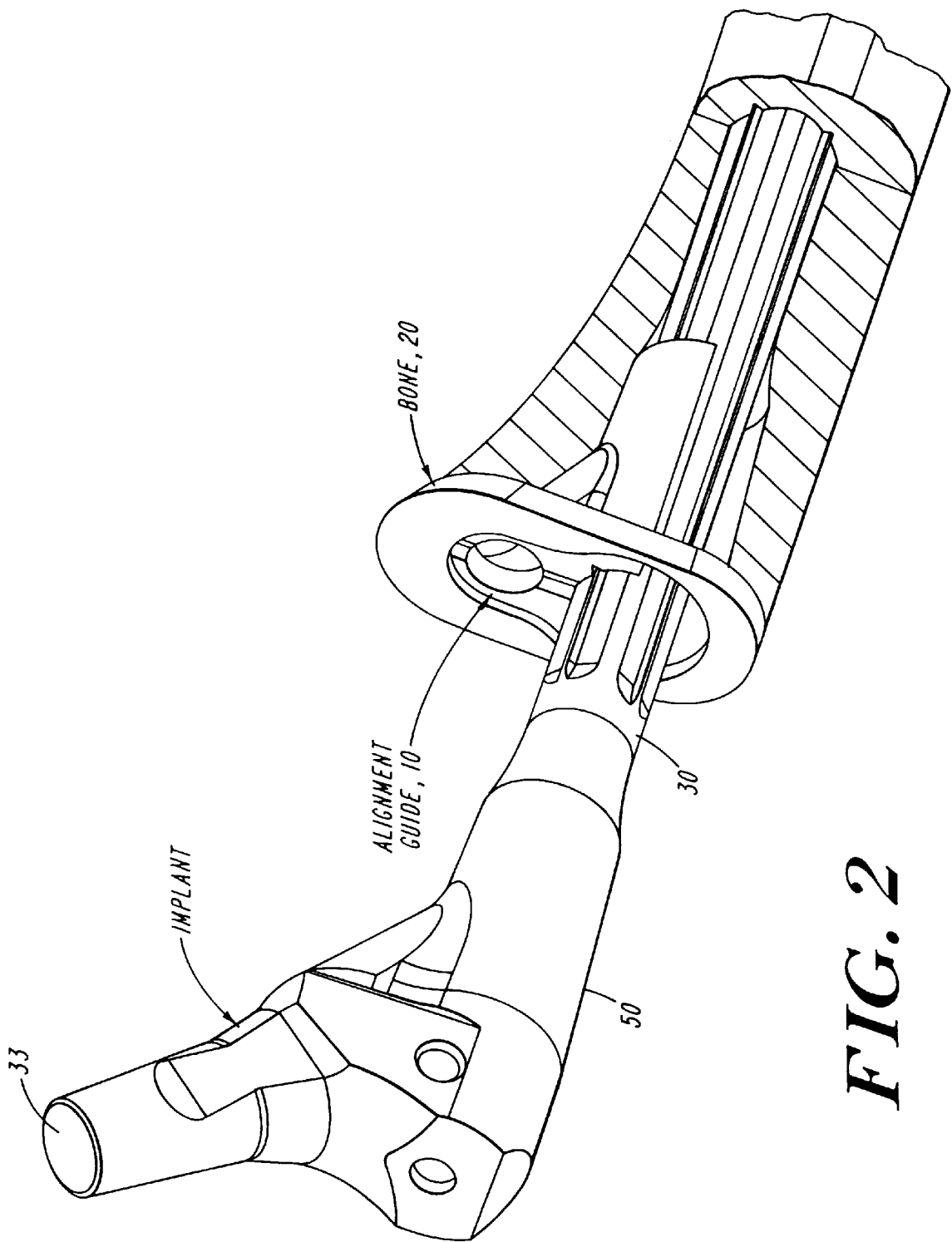
FIG. 2 illustrates a perspective view of the bone, alignment guide and implant of FIG. 1 with the alignment guide in place and the implant inserted partially into the bone through the alignment guide.
Figure 3:
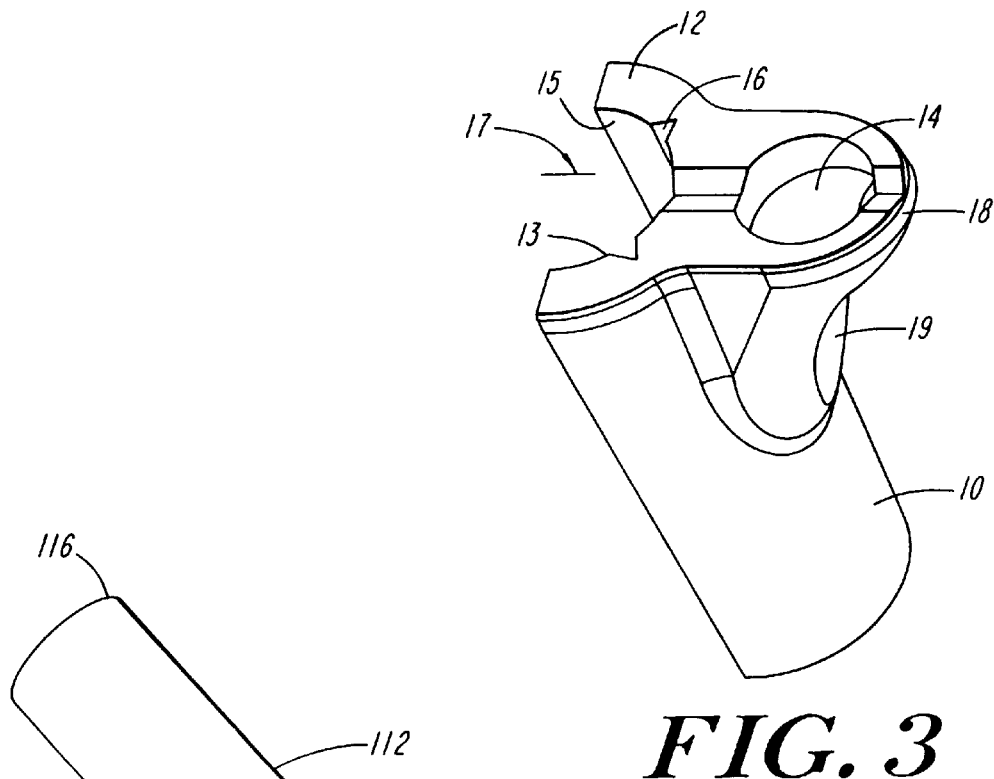
FIG. 3 illustrates a perspective view of the alignment guide of the present invention.

The following is a description of a preferred embodiment of the present invention in use with a hip stem implant. Referring now to FIGS. 1 through 3, an alignment guide 10 is illustrated. The alignment guide 10 comprises a body 11, a guide portion 12, and an opening 14. The body 11 and guide portion 12 form an outer shape that corresponds to at least a portion of a machined cavity 21 in the bone 20. The guide portion 12 has an inner circumference 15 having grooves or notches 16 for receiving flutes 31 of the stem 30 an implant 50. Protrusions 13 in the guide portion 12 may contact the stem 30 of the implant 50. In this embodiment, the grooves 16 and the protrusions 13 form a key for guiding insertion of the stem 30 into the bone cavity. In variations of this embodiment grooves 16, protrusions 13 or the like may be used alone or together to key insertion of the keyed stem 30.

FIG. 1 illustrates a prepared bone 20 having a machined cavity 21 and a longitudinal cavity 22 formed in the canal of the bone. At least a portion of the machined cavity 21 has a shape corresponding to the shape of the alignment guide 10. FIG. 1 further illustrates an implant 50 comprising a stem 30 having flutes 31 distally extending along the length of the stem 30; a protrusion or proximal geometry 32 shaped to fit within the machined cavity 21 of the bone; and a neck 33 extending from the proximal end of the implant for receiving a ball portion of a ball and socket joint.

The notches 16 in the inner circumference 15 of the guide are placed so that when the stem 30 is inserted into the alignment guide 10, the flutes 31 of the stem 30 fit within the notches 16 in the alignment guide 10 to hold or guide the stem 30 in an appropriate or aligned position within the bone cavity.

In this embodiment the shape of the machined bone cavity 21 is generally tapered to form an elliptical end portion 23. The alignment guide 10 is similarly shaped with the body 11 forming an elliptical end portion 18 on the proximal end of the body. The implant 50 as well includes a similarly shaped proximal section with an elliptical end portion 34. The bone cavity 21, further comprises a cut 24 corresponding to tapers 19, 35 on the alignment guide 10 and the implant 50 respectively. The cut 24 of the bone cavity 21 and the taper 19 of the alignment guide 10 prevent the alignment guide 10 from being inserted too far into the bone cavities 21, 22. The cut 24 of the bone cavity 21 and the taper 35 of the implant 50 similarly prevent the implant 50 from being inserted too far into the bone cavities, 21, 22 and thus prevent the neck 33 from being in an improper position.

In use, the alignment guide 10 is inserted into the machined bone cavity 21 with the elliptical end portion 18 of the alignment guide 10 in alignment with the elliptical end portion 23 of the machined cavity 21. The stem 30 of the implant 50 is placed in the inner circumference 15 of the guide portion 12 of the alignment guide 10 with the elliptical end portion 34 of the implant 50 generally in line with a groove 9 across the elliptical end portion 18 of the alignment guide 10. In order to insert the implant 50 properly aligned, the proximal geometry 32 is generally aligned so that it will fit within the machined bone cavity 21. The flutes 31 are placed within the notches 16 of the guide portion 12 and the implant 50 is driven into the bone cavity 22 guided by the alignment guide 10. When the implant 50 is generally in the bone cavities 21, 22 but prior to complete insertion, as illustrated in FIG. 2, the alignment guide 10 is removed by inserting a device into the opening 14 in the guide 10 to remove it from the bone cavity 21 and from the stem 30 of the implant 50. The implant 50 is then further driven into place with the elliptical end portion 34 fitting within the elliptical end portion 23 of the bone and the taper 35 abutting adjacent a cut 24 of the bone cavity 21.

Figure 4:
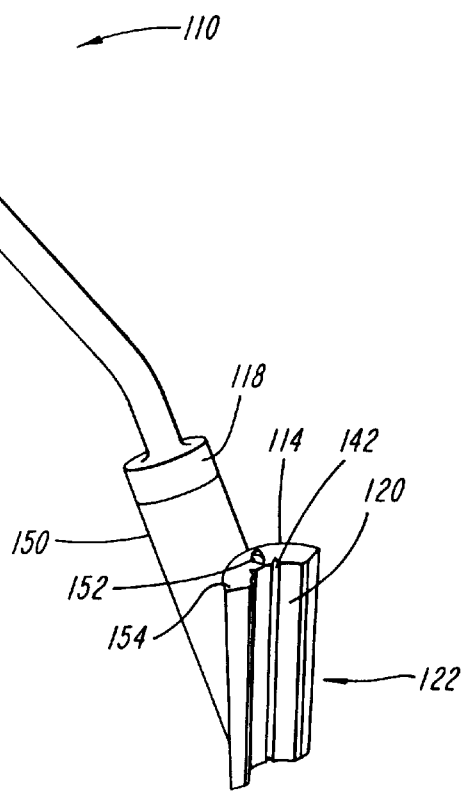
FIG. 4 is a perspective view of an alignment guide of the invention.

An additional alignment guide 110 of the invention, illustrated in FIG. 4, has a handle 112 and an alignment body 114. The handle 112 is generally shaped so as to be easily grasped by a surgeon and has proximal and distal ends 116, 118. The alignment body 114 is located at the distal end 118 of the handle 112 and has a guide surface 120 disposed on an inner portion 122 thereof. The guide surface 120 is releasably engageable with an outer surface 124 of a prosthetic stem 126 as shown in FIG. 5.

The illustrated stem 126 is adapted for use as the femoral component of a hip prosthesis, however, the system of the invention is useful with a variety of prosthetic implants, especially those suited for implantation in a long bone. The prosthetic stem 126 may have proximal and distal portions 128, 130 and have at least one flute 132 formed on its outer surface 124. The distal portion 130 of the stem 126 is substantially cylindrical and may also include a slot 134, in particular, a coronal slot. The proximal portion 128 of the stem may have an angled region 136 or proximal spout having an elliptical cross-section leading to a neck 138. The preparation of a bone cavity (such as bone cavity 21 of FIG. 1) adapted to such a geometry is illustrated in U.S. Pat. No. 4,790,852 to Noiles which is hereby incorporated by reference. A person of ordinary skill in the art will recognize that other reaming or broaching techniques may also be used to create a bone geometry corresponding to the illustrated stem 126.

For use in the present invention, stem 126 has at least one surface element or keyed component, such as flute 132, disposed on its outer surface 124 that is angled with respect to the outer surface 124 and extends in the direction of a longitudinal axis 140 (FIG. 6) of the stem 126. As illustrated in FIGS. 1–2 and 6–8, the stem surface elements may include a plurality of flutes. Generally, these angled surface features 132 may include any combination of indentations or protrusions from the outer surface 124 suitable to hold the stem 126 against rotational misalignment when engaged with the alignment guide 110.

Figure 5:
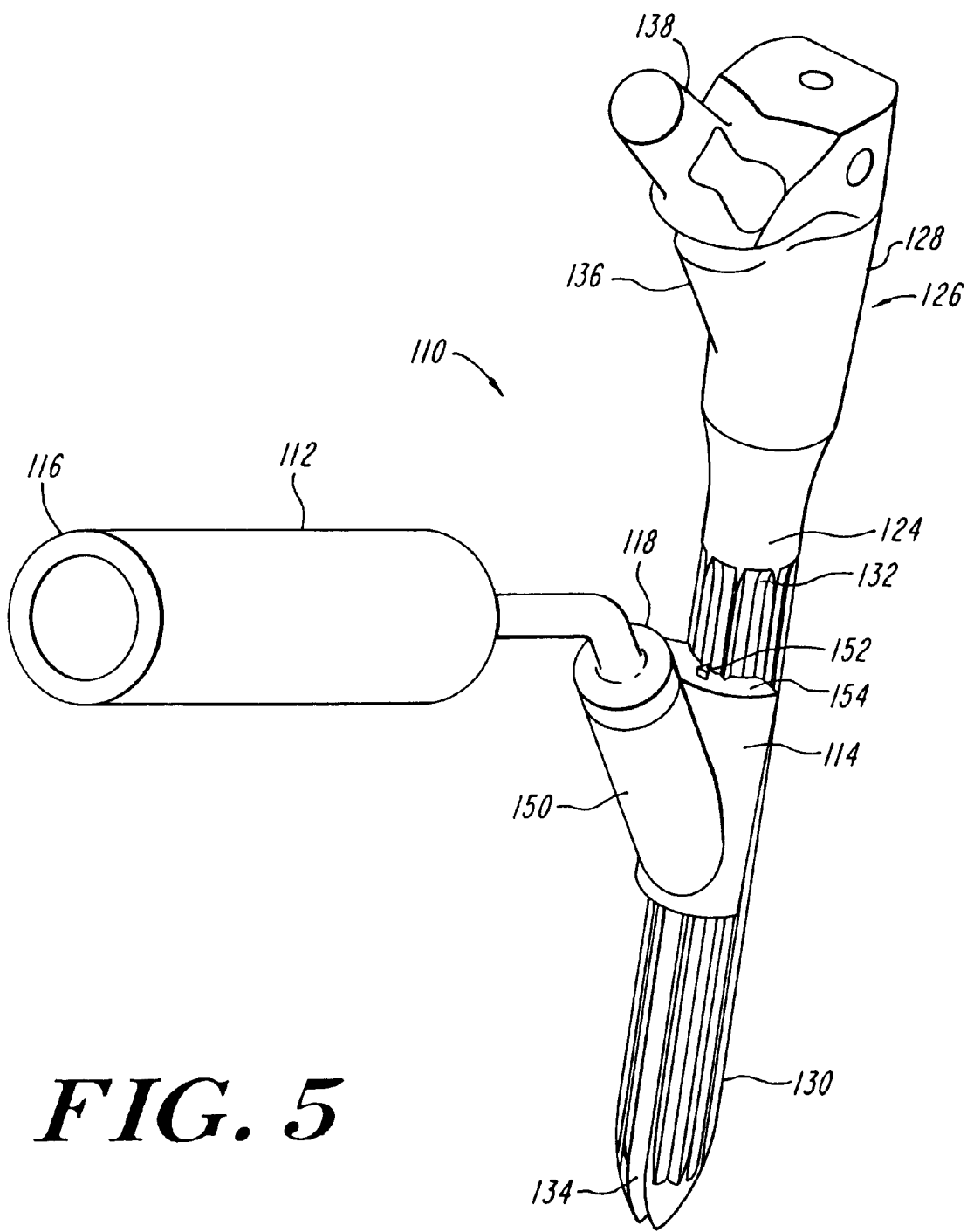
FIG. 5 is a perspective view of the alignment guide of FIG. 4 in contact with a fluted stem of a hip prosthesis femoral component.
Figure 6:
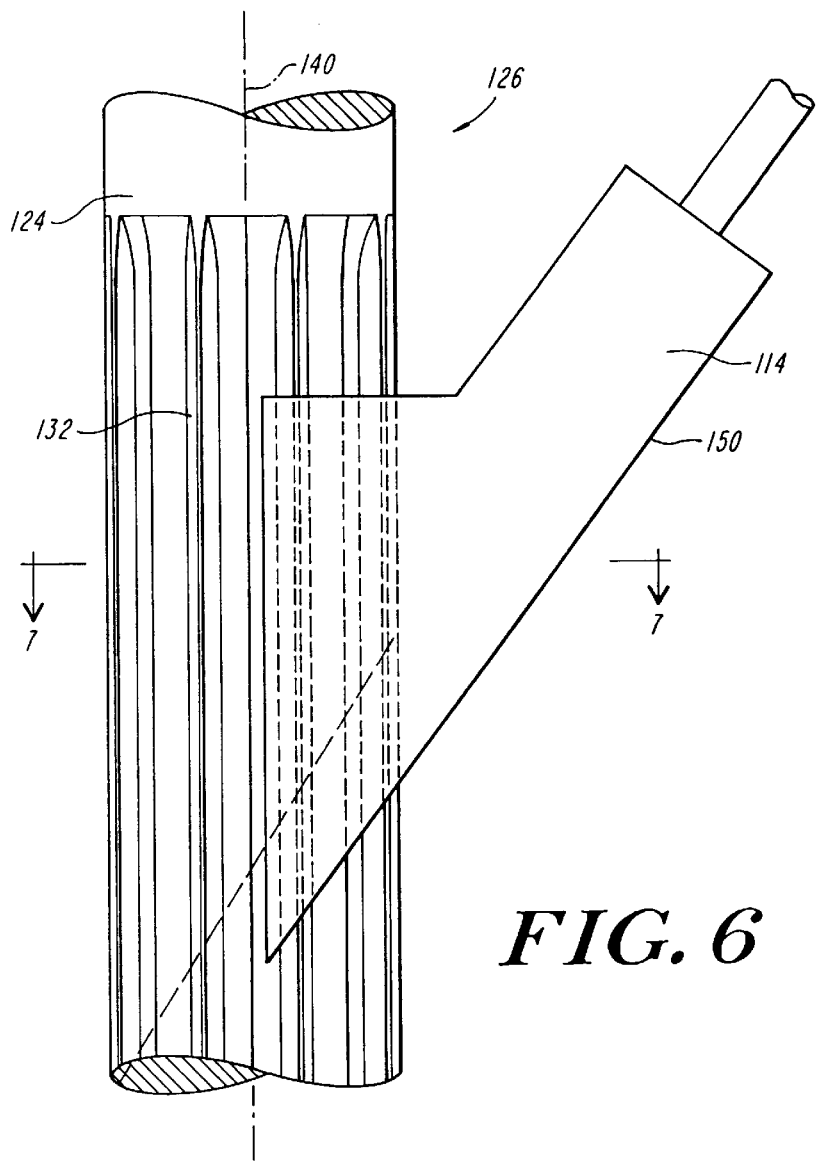
FIG. 6 is a side view of the alignment guide and fluted stem of FIG. 5.
Figure 7:
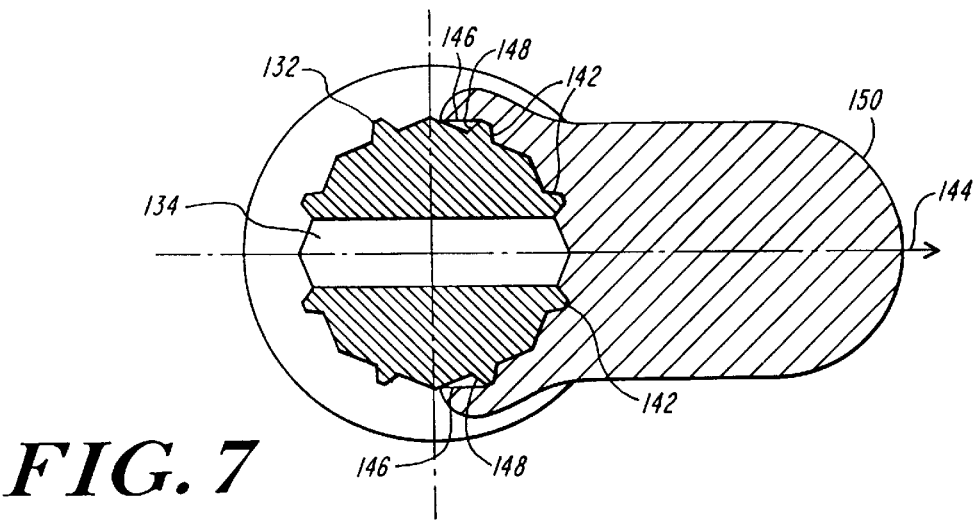
FIG. 7 is a cross sectional view of the alignment guide and fluted stem of FIG. 6 taken along line 7—7.

The guide surface 120 of the alignment guide 110 engages the outer surface 124 of the stem 126, as shown in FIGS. 4–5, around the cylindrical stem 126 generally up to about 180°. The guide surface 120 also includes one or more angled guide surface features 142 which form a key to engage the stem surface features 132 to hold the stem 126 against rotation. The angled guide surface features 142 are also formed so that the guide 110 may be removed from its engagement with the stem 126 in a plane transverse to the longitudinal axis 140 as illustrated by the lateral axis 144 and referred to herein as a lateral direction, which, in the illustrated embodiment, is directed from lateral to medial for a hip prosthesis embodiment.

In the illustrated embodiment, the outermost guide surface features 142 (FIG. 7) each have an outer angled surface 146 formed to allow lateral disengagement. That is, rather than contacting a stem surface feature 132, the outer angled surface 146 is generally in the direction of the lateral axis 144 so as not to engage a lateral facing surface 148 of the stem surface element 132, thus permitting lateral removal of the alignment guide 110 from the stem 126.

In the embodiment illustrated in FIGS. 4 to 8, the alignment guide 110 may have a tapered outer shape 150 to correspond to the shape of the bone cavity into which the stem 126 is being implanted. The alignment guide 110 may also have an alignment marker 152 located on a proximal surface 154 of the guide body 114 to provide a visual aid for engaging the stem 126 with the alignment guide 110.

Figure 8:
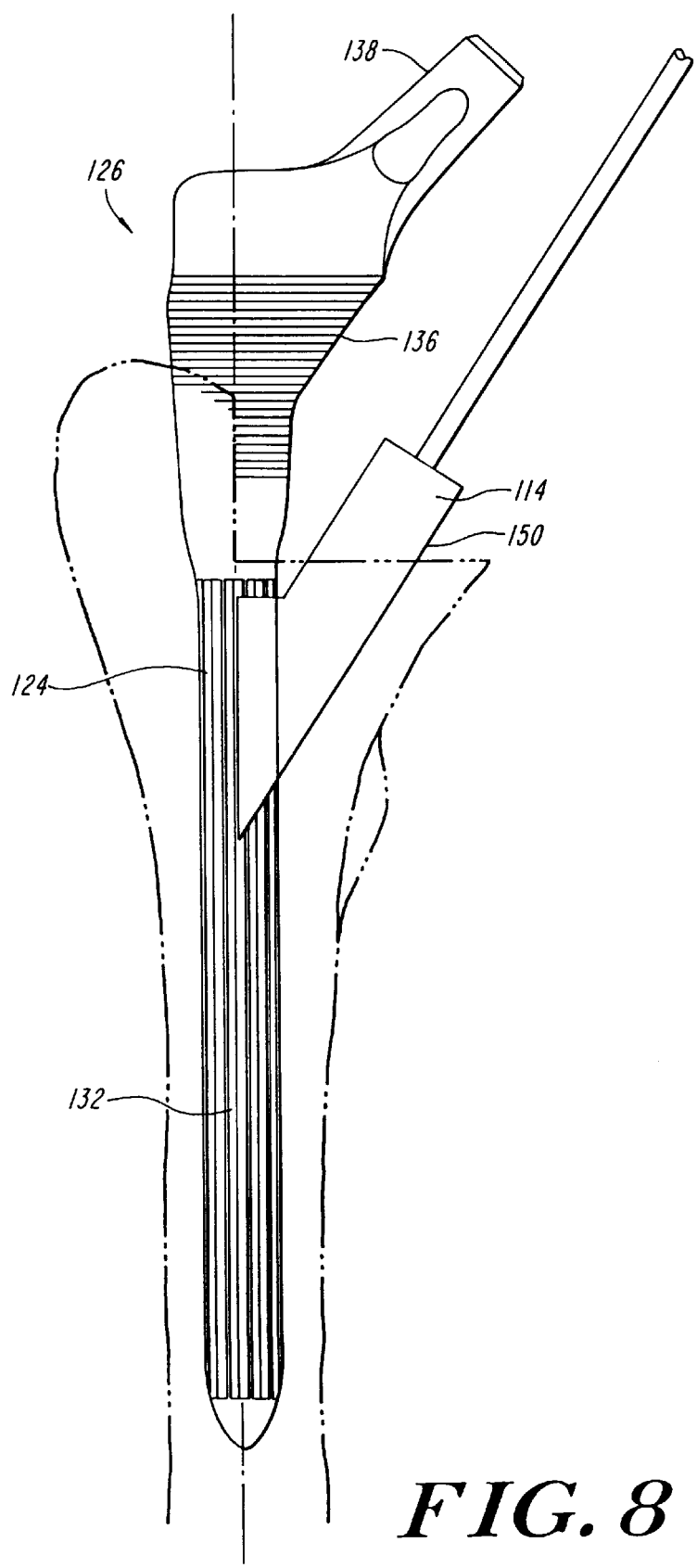
FIG. 8 is a side view of an alignment guide and prosthetic stem component of the invention being inserted into a bone.

A method for inserting a prosthetic stem 126 into a long bone begins with the preparation of a suitable cavity in the long bone. Where, as illustrated in FIG. 8, the stem 126 includes features such as a tapered proximal spout 150, the cavity should be formed so as to correspond to such features.

The prosthetic stem 126 is placed at the opening of the cavity in the long bone in a predetermined rotational orientation and is engaged by the alignment guide 110. The prosthetic stem 126 is inserted into the cavity while maintaining contact with the alignment guide 110. A surgeon may apply lateral pressure using the handle 112 in order to ensure a sufficient engagement between the prosthetic stem 126 and the alignment guide 110 to prevent undesired rotation of the stem 126.

The alignment guide 110 may be removed from the stem 126 prior to final seating of the stem 126 within the cavity. In addition, surface features such as flutes 132 may be longitudinally extended in a proximal direction in the area where the guide 110 meets the stem 126 in order to provide a greater duration of contact between the stem 126 and guide 110.

Although the alignment guide of the present invention is described with respect to a particular embodiment, i.e., in use with a fluted hip stem using the flutes of the stem as a key or reference, it will be apparent to those skilled in the art that various modifications may be made without departing from the character and scope of the invention. For example, the insertion guide may be used to assist the insertion of any stem like component having a keyed feature on the outer surface of the stem to key the insertion of the stem in a properly selected aligned position. The alignment guide may have any number of indentations or protrusions to key in the proper insertion of the stem of the implant.

In particular, further embodiments of the insertion may employ a blade or other protrusion fitted to a slot in the stem to orient and guide the stem into a fitted insertion position. These embodiments allow the stem flutes to be optimized for broaching or cutting a fitted passage and securing the stem to the bone without requiring the flutes to also sustain shear forces imposed during insertion by a guiding surface. As seen in FIG. 5, a suitable slot 134 may be already provided on some stems, and this slot is generally oriented to reduce stem stiffness along one direction, while allowing some flexibility of fit of the distal stem as it enters the prepared bone bore.

Figure 9:
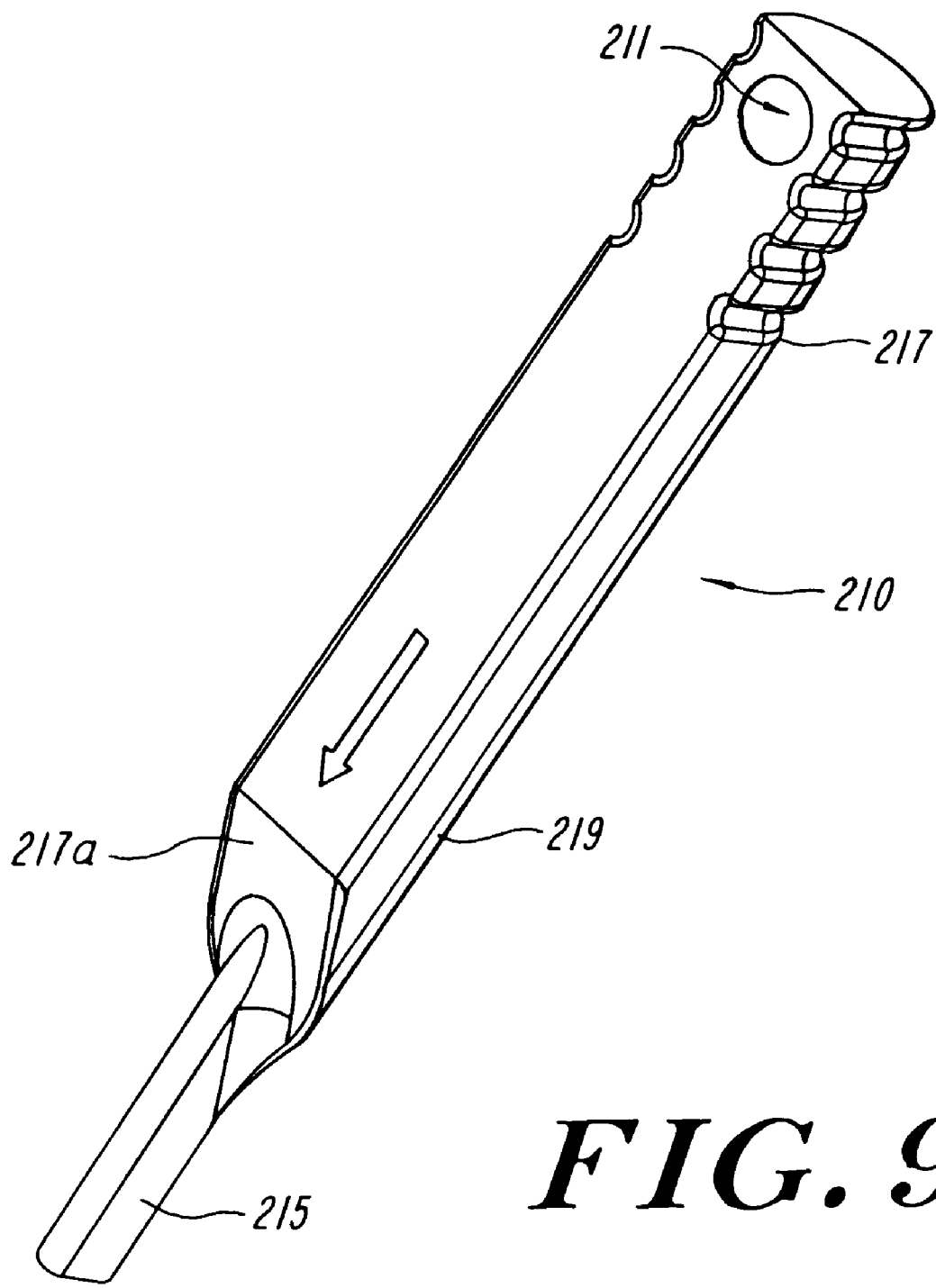
FIG. 9 is a perspective view of another alignment guide of the invention.

FIG. 9 illustrates an alignment guide 210 of the invention configured for slot engagement. In this embodiment, the guide has a blade 215 which protrudes from one end of a handle 217, which as illustrated is provided with gripping features such as knurling, finger grooves or the like. An intermediate portion of the guide has a surface 219 shaped to nest or fit within the prepared curved and inclined spout bore of the resected bone end, e.g., against surface 24 (FIG. 1). Surface 219 thus orients blade 215 along a central parallel plane. Similarly the prosthesis slot precisely fits the blade, and is oriented along a central plane of symmetry of the prosthesis post and shoulder, so that the prosthesis is thus oriented to seat correctly when fully inserted.

As further illustrated in FIG. 9, the main body of the handle 217 has a distal end face 217*a* which crosses the handle longitudinal axis substantially parallel to the bone insertion axis, i.e., at an angle of about 30° corresponding to the angle between the bone canal axis and the axis of the prepared bone spout bore. This allows the prosthesis stem to slide along the blade 215 close to and substantially parallel to the face 217*a*, providing maximum strength, rigidity and precision of the guide mechanism. By way of example, the thickness of blade 215, and the corresponding stem slot width, may be on the order of 2–5 millimeters. The handle may be 10–15 centimeters long, with the blade extending an additional 1–4 centimeters, preferably resulting in a relatively short, maneuverable guide with a total length under about 14 centimeter. The guide is advantageously machined or fabricated of a solid metal, such as titanium or a stainless steel or surgical alloy.

Figure 10:
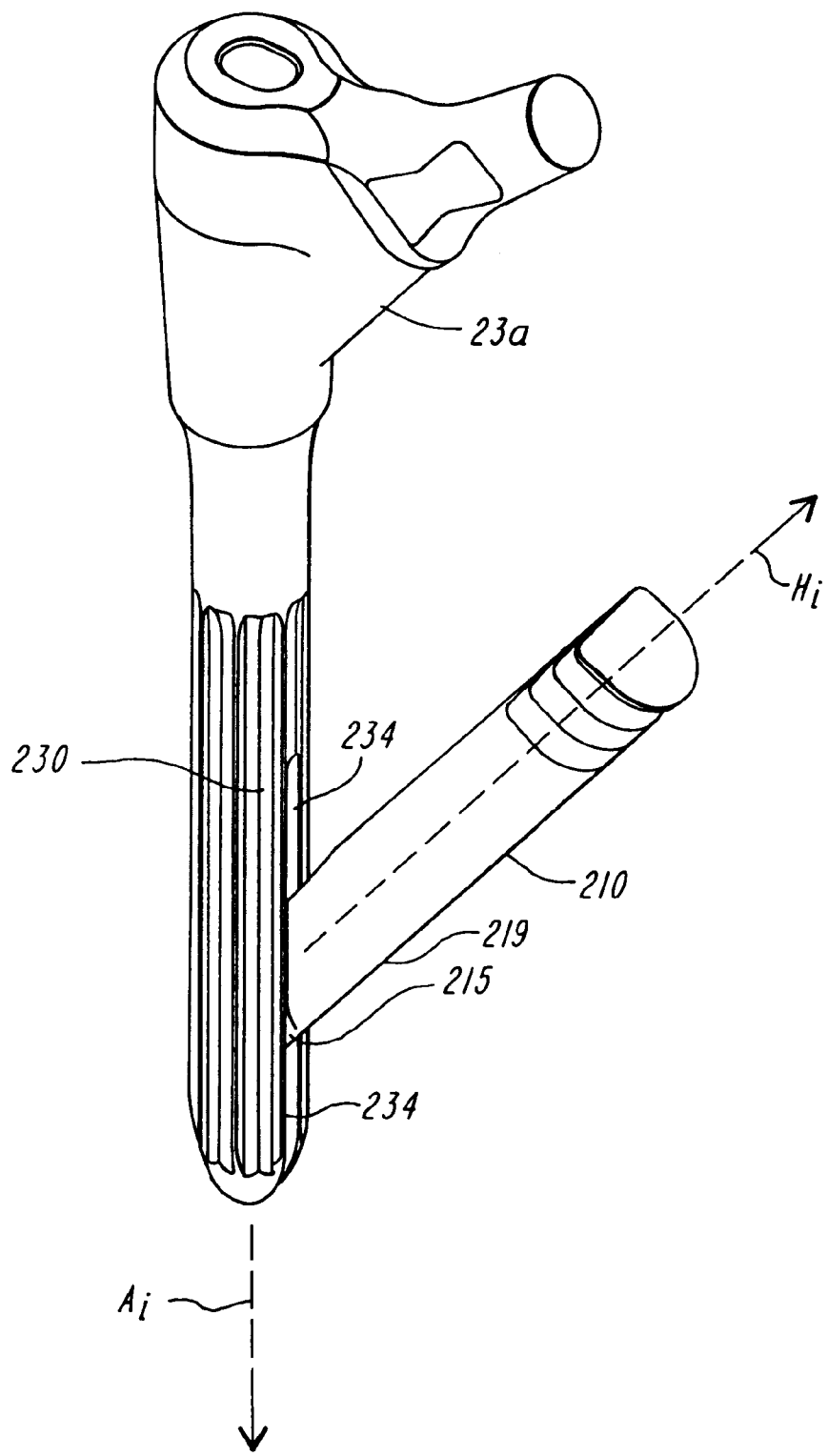
FIG. 10 is a view of the guide of FIG. 9 engaging a prosthetic stem.

FIG. 10 shows the guide of FIG. 9 in engagement with a prosthesis stem 230 similar to the stem of FIG. 5. As shown, the blade 215 fits precisely in slot 234, thus aligning and centering the prosthesis surface 239 with guide surface 219. As the stem is inserted in bone along an insertion axis A, the blade 215 rides up the slot 234. Once the stem is securely tracking as it is inserted in the bone the blade 215 may be withdrawn along the direction of the handle axis $H_i$. For ease of withdrawal, the handle has grip-enhancing features at its proximal end, and is also provided with a cross-hole 211 (FIG. 9) which may receive a T-bar or be engaged by an engagement hook of an impact puller, to exert a withdrawal force along axis $H_i$.

As noted above, in existing slotted stem prostheses, the slot serves a compliance function allowing a reduction of bending stiffness; it may also be compressed as the stem tip is driven in and subjected to radial compressive force. To prevent binding of the guide in the stem as the slot is closed, it is therefore desirable to fabricate the blade or slot with this added consideration in mind. For example, width dimensions may be set to initially achieve a slight clearance therebetween, such that as the distal tip commences to cut its way along the machined bone canal, the two components acquire a precise fit. Alternatively, the slot may taper wider toward the stem proximal end to facilitate withdrawal once the stem has been sufficiently inserted. Similarly, the blade to stem contact area may be reduced, for example by hollow-grinding the central face of the blade, so that despite high compressive forces the blade may slide along the slot and be easily withdrawn. Furthermore, in conventional prostheses, such as titanium prostheses, the slot extends only partially up the distal stem, and this slot length may be inadequate for achieving a sufficiently stable insert direction before the blade has to be withdrawn. In the prototype alignment guide shown in FIG. 9, the distance during which the stem remains precisely guided during insertion is made long or maximized by positioning the blade vertically offset along the stem insertion axis—i.e, by having it project from the lower portion of the handle cross section. This limitation may also be addressed by providing a slot 234 which extends further up the prosthesis stem, a procedure which may be readily implemented for stiffer, stronger prosthesis alloys such as cobalt chrome. In other embodiments, the distal stem flutes are made slightly larger in diameter to assure sufficient bite in the bone canal early in insertion to guarantee straight insertion after being guided only a short distance by the alignment tool. Thus, blade offset and stem and slot width and length may each be adjusted to assure that the blade functions as an effective guide.

Figure 11A:
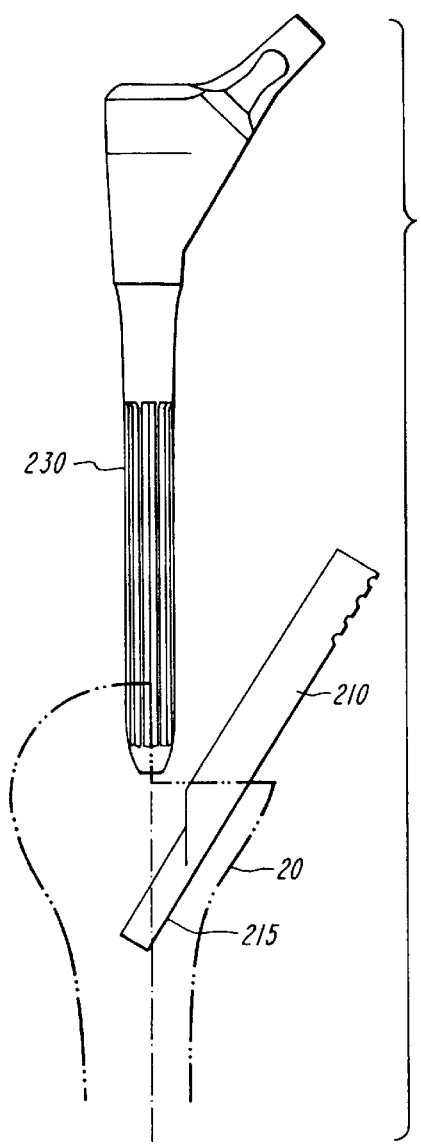
FIGS. 11A and 11B illustrate stem insertion with the guide of FIG. 9 in a prepared bone.
Figure 11B:
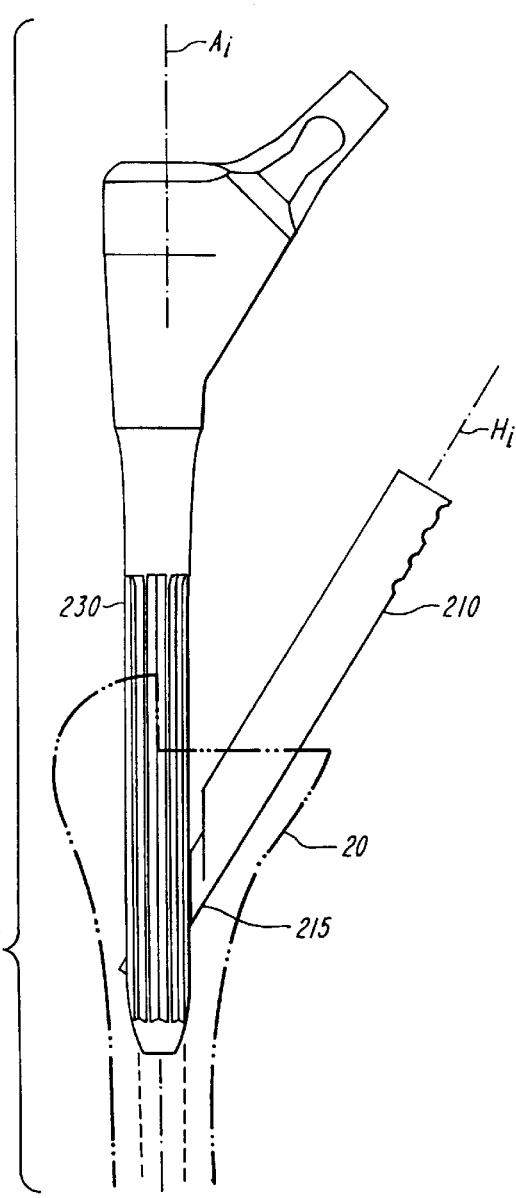

FIGS. 11A and 11B illustrate the use of the alignment guide 210 of FIG. 9. As shown in FIG. 11A, the guide is nested against the cylindrical prepared surface of the angularly oriented spout channel machined in the proximal femur 20, and the prosthesis stem 230 is lowered over the blade 215 while care is taken to visually align the stem along the axis of the bone. Thereafter, the stem is driven into the bone, while the blade 215 provides a firm and precise guide surface, constraining the stem of the prosthesis in the desired guide plane while allowing straight movement deeper into the bone canal.

Figure 12:
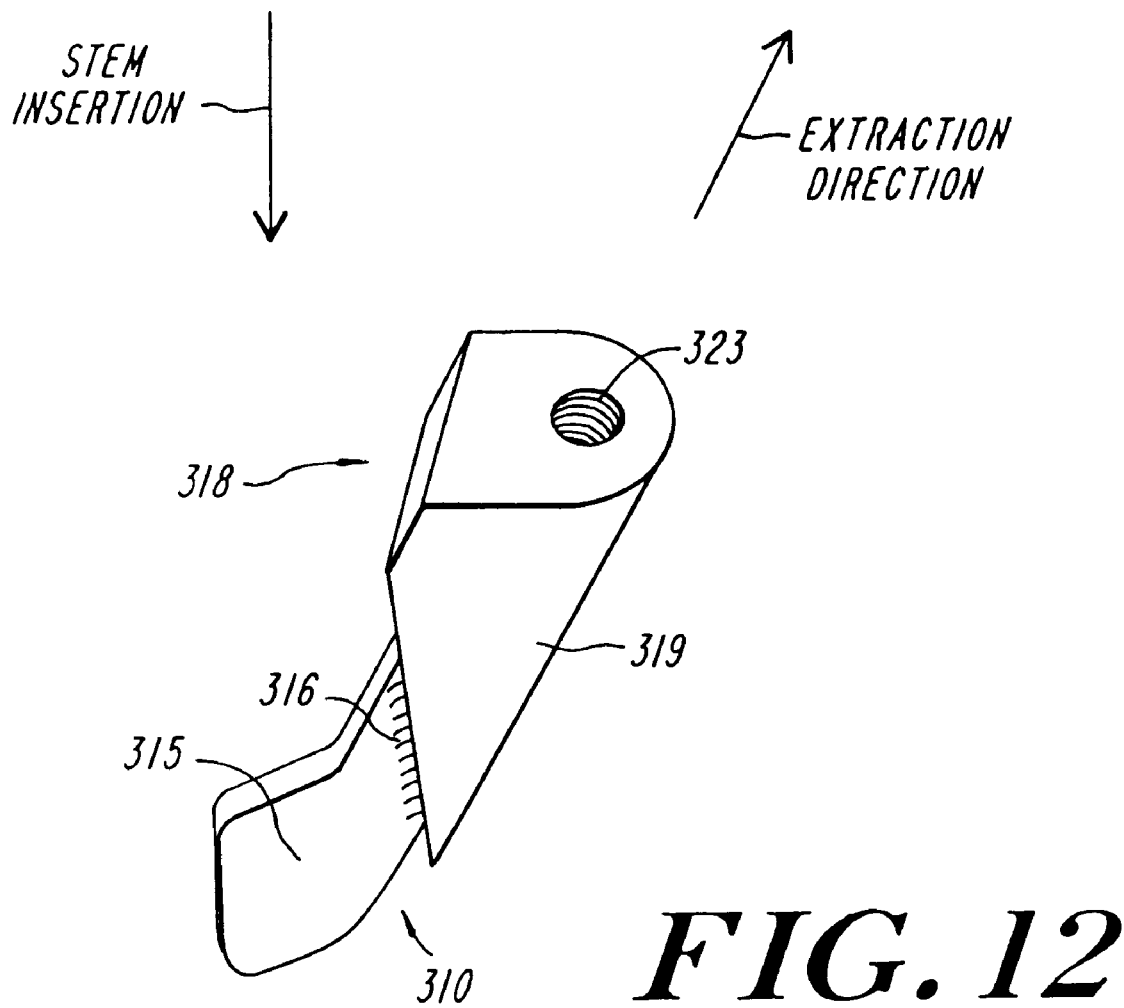
FIG. 12 illustrates another alignment guide.

In addition to the embodiment of FIG. 9, the present invention contemplates an embodiment of the alignment guide wherein a structure corresponding to the hand-grip portion of the handle is optional, and, if provided, is a separate element or tool of the system. In this embodiment, an essential portion of the guide includes only a body that seats in a defined orientation against the prepared bone surface, and that possesses a blade protruding therefrom and positioned across the central plane in which the stem alignment slot is to be positioned. Such an alignment guide embodiment 310 is shown in FIG. 12. As seen therein, the guide possesses a slot-engaging blade 315 that extends radially across the bone canal from the edge of an arm 316, which in turn extends downwardly from a positioning body 318. As in the embodiment of FIG. 1, the positioning body 318 possesses a surface 319 which aligns against a prepared bone surface. It also has a gripping hole 323 for attaching a handle or extractor to allow removal of the body 318 along an extraction direction parallel to the spout bore, after the stem has been inserted to a substantial depth.

This completes a description of the invention and representative embodiments thereof. Having been thus disclosed, further variations and modifications will occur to those skilled in the art, and all such variations and modifications are considered to be within the spirit and scope of the invention, as defined by the claims appended hereto and equivalents thereof.

What is claimed is:

1. An alignable orthopedic prosthesis system for implantation into a prepared bone cavity, said system comprising:
   (a) a prosthesis including a stem having a proximal portion, a distal portion, and an axis, with a slot extending along the axis of the stem, and
   (b) an alignment guide including
      an alignment handle having an outer shaped surface portion corresponding to at least a portion of the prepared bone cavity, and
      a guide blade disposed on an inner portion of the alignment handle and keyed for engaging the slot of the stem, said outer shaped surface portion being positioned such that when said shaped portion seats against the prepared bone cavity, the blade is located in a plane effective to fix rotational alignment of the stem while allowing sliding insertion, such that the guide blade orients the prosthesis to seat in a desired orientation in the bone.

2. The prosthesis system of claim 1, wherein the prosthesis comprises a stem of a prosthetic joint assembly.

3. The prosthesis system of claim 2, wherein the blade comprises at least one relief portion for reducing binding in the slot.

4. The prosthesis system of claim 2, wherein the blade effectively fills the cross-section of the slot.

5. The prosthesis system of claim 3, wherein the blade extends transverse to the stem.

6. The prosthesis system of claim 1, wherein the alignment guide further comprises means for effecting removal of the guide from the stem along an axis parallel to or a direction away from the prepared bone cavity.

7. The prosthesis system of claim 1, wherein the proximal portion of the stem comprises a proximal geometry shaped to fit said prepared bone cavity.

8. The prosthesis system of claim 1, wherein the outer shaped surface portion fits against a cylindrical prepared bone surface to align the blade along an axis.

9. The prosthesis system of claim 8, wherein the handle and blade of the alignment guide both extend along said axis.

10. A prosthetic stem system comprising:
    (a) a prosthetic stem including a longitudinal axis, a slot extending along the axis, and an outer surface having at least one stem surface feature extending along the outer surface in a substantially longitudinal direction for penetrating and gripping bone, and
    (b) an alignment guide including:
       a handle having proximal and distal ends and a longitudinal axis;
       an alignment blade disposed on the distal end of the handle to releasably engage the slot as a guide surface that extends parallel to the handle across the longitudinal axis to engage inside slot surfaces and provide rotational stability to the prosthetic stem during insertion of the stem into a bone,
    said alignment guide being oriented by contact with a prepared bone surface to guide the slot during prosthesis insertion to fit a final insertion position.

11. The stem system of claim 10, wherein the stem is fluted.

12. The stem system of claim 10, further comprising a femoral prosthesis associated with the prosthetic stem, the femoral prosthesis including a spout, wherein the blade is oriented to be in a plane aligned with the spout of the femoral prosthesis.

13. The stem system of claim 10, wherein the blade is laterally disengageable from the stem by movement along the longitudinal axis of the handle.

14. The stem system of claim 10, wherein the stem is elongated, substantially cylindrical and implantable within a prepared bone cavity of a long bone.

15. The stem system of claim 14, wherein the stem forms at least part of a femoral component for a hip prosthesis.

16. The stem system of claim 15, wherein the stem includes a proximal spout.

17. The stem system of claim 14 wherein the alignment guide handle comprises an outer surface shape corresponding to at least a portion of the prepared bone cavity for orienting the blade.

18. The stem system of claim 14, wherein the slot provides bending fit of the stem, and the slot tapers wider toward a proximal end of the slot to reduce binding on the blade.

19. A method for inserting a prosthetic stem into a long bone comprising the steps of:

(a) preparing a cavity in the long bone;
(b) providing a prosthetic stem having a longitudinal axis, an outer surface, and at least one stem slot extending along a longitudinal direction
(c) providing an alignment guide including a handle having proximal and distal ends, and an alignment blade disposed on the distal end of the handle and releasably engageable with the slot of the prosthetic stem, wherein the blade rigidly projects from the handle so as to fit in the slot and engage the stem to provide rotational stability to the prosthetic stem
(d) placing the alignment guide at the prepared cavity so as to orient the blade in a predetermined rotational orientation
(e) engaging the alignment guide blade in the slot of the prosthetic stem, and
(f) inserting the prosthetic stem into the cavity along the blade, thus guiding the stem into a final position fitting the prepared cavity.

* * * * *

UNITED STATES PATENT AND TRADEMARK OFFICE
CERTIFICATE OF CORRECTION

PATENT NO. : 6,174,335 B1  
DATED : January 16, 2001  
INVENTOR(S) : Michael Varieur et al.

Page 1 of 1

It is certified that error appears in the above-identified patent and that said Letters Patent is hereby corrected as shown below:

<u>Title page,</u>
References Cited, U.S. PATENT DOCUMENTS, before the line beginning
"4,347,845 * 9/1982 Mayfield ..... 606/86", insert the lines
-- 3,857,389 * 12/31/74 Amstuz .....   128/92EC --.

References Cited, U.S. PATENT DOCUMENTS, before the line beginning
"4,738,256 * 4/1998 Freeman et al. ..... 606/87", insert the lines
-- 4,475,711 * 07/12/88 Mäi.......... 623/2 --.

References Cited, U.S. PATENT DOCUMENTS, before the line beginning
"5,409,492 * 4/1995 Jones et al. ..... 606/86", insert the lines
-- 4,936,863 * 06/26/30 Hofmann.......... 623/23 --.

References Cited, U.S. PATENT DOCUMENTS, before the line beginning
"5,480,453 * 1/1996 Burke ..... 623/23", insert the lines
-- 5,480,452 * 01/02/96 Hofmann et al. 623/23 --.

References Cited, before the line beginning "*cited by examiner", insert the lines
-- FOREIGN PATENT DOCUMENTS
    2627380 * 2/1988 France..........................2/30
    0850610 * 12/1997 Europe..........................2/46

Signed and Sealed this

Eighth Day of January, 2002

*Attest:*

JAMES E. ROGAN  
*Attesting Officer*     *Director of the United States Patent and Trademark Office*